United States Patent [19]
Jeffers

[11] Patent Number: 4,609,875
[45] Date of Patent: Sep. 2, 1986

[54] CORONA DISCHARGE FREON GAS SENSOR HAVING ELECTRICAL WIND PUMPING ACTION

[76] Inventor: Edward A. Jeffers, 1010 E. 31st St., Hialeah, Fla. 33013

[21] Appl. No.: 526,613

[22] Filed: Aug. 26, 1983

[51] Int. Cl.$^4$ ............................................. G01N 27/60
[52] U.S. Cl. ........................................ 324/455; 73/23; 324/464; 361/230; 361/233
[58] Field of Search ................ 324/72, 455, 464, 457; 73/23; 340/632; 422/83, 98; 436/153; 361/230, 233

[56] References Cited
U.S. PATENT DOCUMENTS
3,449,667  6/1969  Gourdine ............................ 324/464

FOREIGN PATENT DOCUMENTS
646241  2/1979  U.S.S.R. ............................. 324/455

Primary Examiner—Reinhard J. Eisenzopf
Assistant Examiner—Kevin D. O'Shea
Attorney, Agent, or Firm—Ernest H. Schmidt

[57] ABSTRACT

A halogen gas detector employing the negative corona principal is equipped with a corona discharge sensing tip utilizing the "electrical wind" phenomenon of field corona discharge to create a continuous flow of the gas sample being sensed through the corona, thereby ensuring that virtually every molecule of halogen gas impurity comes into contact with the corona discharge for dependable, uniform, and substantially instantaneous gas sensing operation.

8 Claims, 6 Drawing Figures

U.S. Patent    Sep. 2, 1986    4,609,875
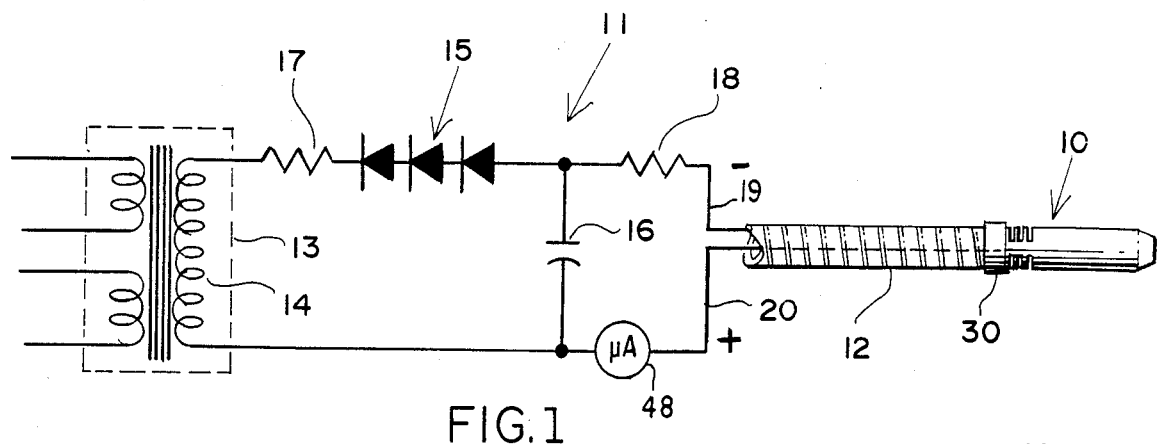
FIG. 1
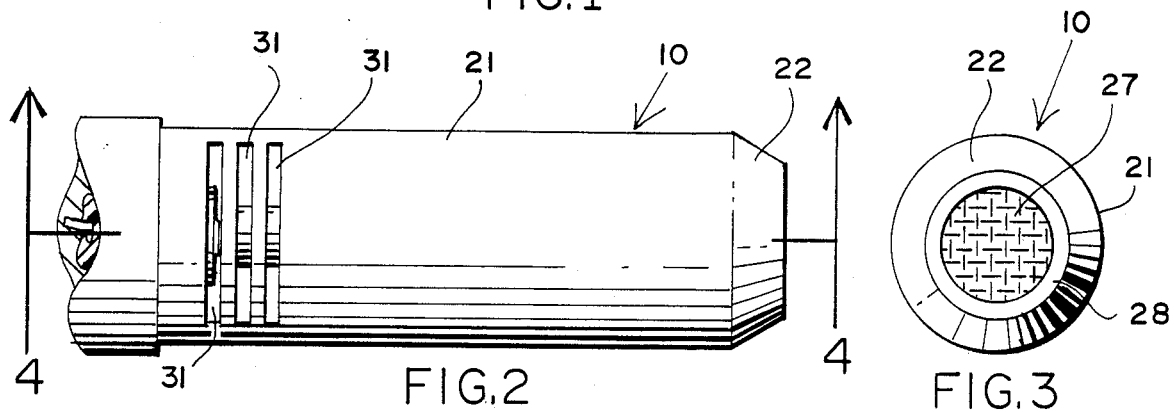
FIG. 2    FIG. 3
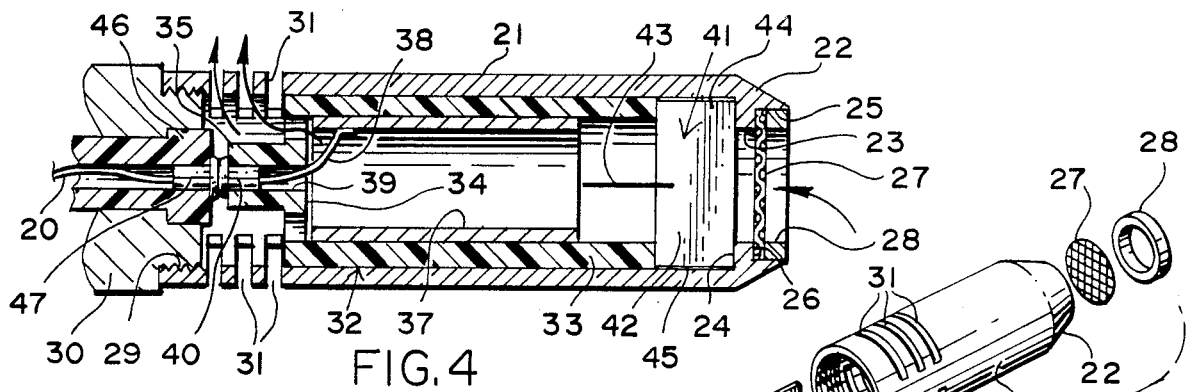
FIG. 4
FIG. 5
FIG. 6

CORONA DISCHARGE FREON GAS SENSOR HAVING ELECTRICAL WIND PUMPING ACTION

BACKGROUND OF THE INVENTION

In the installation and servicing of air conditioning equipment using freon as the refrigerant, a means of detecting freon gas leakage from the system is a practical necessity. Among the various methods and apparatus heretofore devised for conveniently detecting the leakage of small quantities of freon refrigerant gas into the surrounding atmosphere, negative corona electrical sensing devices have been found to be especially efficient, sensitive, and easy to use. Such instruments are based in theory on the work of Weissler & Mohr, Physical Review, Vol. 72, No. 4, Aug. 15, 1947, pp. 294–297, wherein the effect of substantial lowering of a negative corona discharge current by the introduction of freon in minute quantities into the corona atmosphere is described in detail. In Gazov, Khromatogr. No. 3, 61-6 (1965) (Russ)., V. M. Partispanyan, A. V. Markevich, and S. L. Dobychin describe, in a scientific article titled "Use Of A Negative Corona Discharge For Detecting Gases" how halogen gases in minute quantities remarkably decrease corona discharge current. As an example of a practical freon gas leak detector based on the work of Weissler and Mohr and the Russian scientists, reference can be made to applicant's patent application titled HALOGEN GAS LEAK DETECTOR, Ser. No. 06/304,483, filed Feb. 22, 1981, issued as U.S. Pat. No. 4,488,118. Typically, such halogen or freon gas leak detectors utilize a sensing tip which is projected into the ambient atmospheric zone to be tested or sensed for freon gas contamination indicative of leakage. The sensing tip comprises a small protective shell, constituting the anode electrode, surrounding a point cathode energized by the hand-held body of the instrument to establish a negative corona within the protective shell. Slots or holes provided in the protective shell allow diffusion of the gas molecules into the corona discharge for effecting corona current changes in the presence of freon gas molecules. These current changes activate audio or visual alarms indicating the presence of atmospheric halogen or freon gas contamination or leakage to the operator.

Since the migration of the gaseous atmosphere being sensed through the slots or holes of the protective and corona sustaining shell is slow and often dependent on local air current or wind conditions in the vicinity, the sensing of freon gas contamination is often slow and erratic. In attempts to overcome this disadvantage, small air pumps of one kind or another have been utilized to draw atmospheric air into the protective shell openings and through the corona. This expedient of providing external mechanical means of creating a steady flow of gas to be sampled through the corona is deficient in several respects, principally in that it requires the expenditure of a substantial increase in electrical energy, while at the same time increasing the size of the apparatus, both features of which are undesirable, particularly in hand-held or portable instruments.

SUMMARY OF THE INVENTION

It has been known for a long time that if a corona discharge is set up at the end of a sharp electrode, a stream of air can be felt in the vicinity of the discharge. This "electrical wind" or "ion wind" blows from the pointed cathode electrode, along the electric field lines of force, as the moving ions in the discharge transfer momentum to the surrounding as molecules. It is, accordingly, the principal object of this invention to provide a sensing tip for negative corona freon gas sensing devices that obviates the above-described deficiencies of known sensing tips heretofore utilized by making use of the "electrical wind" phenomenon of corona discharge to create a continuous flow of the atmospheric air to be sensed through the corona gap.

A more particular object of the invention is to provide a novel and improved sensing tip for corona discharge or ionization type halogen or freon gas detectors that includes spaced, through openings therealong for continuous flow of the atmospheric air being sensed through the corona, as influenced by the "electrical wind" initiated at the end point of the highly stressed corona cathode electrode.

Another object of the invention is to provide a self-venting sensor tip of the character described wherein the electrode pair defining the corona gap comprises an externally electrically insulated cartridge replaceably received within a protective metal shell having an entrance opening at the front and vent openings at the back, the electrode pair further comprising a sharp-tipped cathode wire coaxial with a cylindrical shell anode and so directed and spaced that the "electrical wind" is drawn through the front opening, through the corona and vented through the rear openings in the exterior metal shell.

Other objects, features and advantages of the invention will be apparent from the following description when read with reference to the accompanying drawings.

BRIEF DESCRIPTION OF THE DRAWINGS

In the drawings, wherein like reference numerals denote corresponding parts throughout the several views:

FIG. 1 illustrates how an improved corona discharge sensing tip embodying the invention connects with and is energized by the high voltage corona-producing electrical circuitry;

FIG. 2 is a side elevational view of the sensing tip, together with a portion of the flexible conduit fitting with which it connects, all on an enlarged scale;

FIG. 3 is a front elevational view of the outer end of the sensing tip shown in FIG. 2;

FIG. 4 is a longitudinal cross-sectional view of FIG. 2, taken along the lines 4—4 thereof in the direction of the arrows, illustrating constructional details of the sensing tip and its associated flexible conduit connector fitting;

FIG. 5 is an "exploded" view of the sensing tip and portions of the flexible tip connector fitting; and FIG. 6 is an oblique view of the replaceable tip electrode cartridge, shown separately.

DESCRIPTION OF THE PREFERRED EMBODIMENT

Referring now in detail to the drawings, reference numeral 10 designates, generally, a corona discharge sensing tip embodying the invention, energized by high voltage corona-producing circuitry indicated schematically at 11 through a flexible conduit 12 at the outer end of which said tip is replaceably secured and electrically connected in the manner hereinafter described. The energizing circuitry 11 may conveniently comprise, for the purpose of providing the high voltage at low current needed to establish the tip corona, a blocking oscillator transformer 13 the high voltage secondary winding 14 pulsating output voltage of which is rectified by half-wave diode rectifiers 15 in conjunction with filter capacitor 16 and series resistor 17.

The rectified high voltage is fed through current limiting resistor 18 and flexible conduit 12 to the corona discharge sensing tip 10. To this end, the negative potential high voltage conductor 19 connects with the flexible outer metallic casing of the flexible conduit 12 to connect with the tip cathode or emitter wire, and the positive potential high voltage conductor 20 extends centrally through said conduit to connect with the tip cathode, as is hereinafter more particularly described. Since the energizing circuitry for the blocking oscillator transformer 13 is known to those skilled in the art and forms no independent part of this invention, it is not deemed necessary to further illustrate and describe such energizing circuitry. Suffice it to say that the blocking oscillator transformer 13, its associated input exitation circuitry and the high-voltage output circuitry hereinabove described for supplying the sensing tip corona voltage can be assembled into a hand-held apparatus, self-powered by a battery of small dry cells.

Referring now to FIGS. 2, 3 and 4, the sensing tip 10 comprises a metallic, tubular outer shell 21, preferably of aluminum, the outer end of which is frusto-conically tapered as indicated at 22. The interior of the shell frusto-conical portion 22 is formed with an interior peripheral wall portion 23 of reduced diameter defining an interior annular shoulder 24. The interior peripheral wall 23 opens at the outer end to an increased-diameter interior wall portion 25 defining an outer annular seat 26. Seated against the outer annular seat 26 is a wire mesh screen disc 27, secured in place by an annular ring 28 press-fitted within the recess defined by interior wall portion 25. The opposite or inner end of the tubular outer shell 21 is internally threaded, as indicated at 29, for screw-on interconnection with a threaded male connector fitting 30 secured at the outer end of the flexible conduit 12. A plurality of diametrically-opposed, transverse slots 31 are cut through the tubular outer shell 21, near the inner end thereof, for discharge flow of the air being sensed for freon or halogen gas contamination as is hereinabove more particularly described.

Removably received within the tubular outer shell 21 is a sensing tip cartridge 32. (see FIG. 6) The sensing tip cartridge 32 comprises a tubular casing 33, molded or machined of electrical insulating material such as Nylor or Teflon, the outer diameter of which is such as to provide for slide-fit within the tubular outer shell 21. As illustrated in FIG. 4, the inner end of the tubular casing 33 is closed by an end wall portion 34. The end wall portion 34 is integrally formed with a coaxial, outwardly-extending, cylindrical projection 35 of substantially reduced diameter. The annular zone of end wall portion 34 between the projection 35 and the inner diameter of the tubular casing 33 is provided with a plurality of circularly-spaced openings 36 for the through flow of air being sensed for halogen gas or freon contamination.

Slidingly received within the cylindrical cavity of sensing tip cartridge tubular casing 33 is a tubular metal anode sleeve 37, which is preferably fabricated of brass and is retained in place by friction fit. An electrical conductor 38 soldered or otherwise electrically connected within the interior of the anode sleeve 37 near the inner end thereof, extends through a central through opening 39 in the projection 35 to pass through the central opening of a contactor ferrule 40 press-fitted within the outer end of said projection. The outer end of the electrical conductor 38 is secured to the brass or copper ferrule 40 as by soldering, thereby further mechanically securing the anode sleeve 37 in place and at the same time providing for its energization through flexible conduit connector fitting 30.

The sensing tip cartridge 32 further comprises a cathode assembly 41 comprising a rectangular metal plate 42, mechanically and electrically secured with respect to one side of which, and projecting outwardly perpendicularly of a longitudinal edge thereof, is a small diameter cathode wire 43. A cathode wire of Nichrome having a diameter of approximately 0.001 inches and cut to a point at its outer end has been found to have superior emitter characteristics for establishing of the negative corona. Diametrically-opposed slots 44, 45 in the outer end of the sensing tip cartridge casing 33 serve to frictionally receive and seat outer end portions of the rectangular metal plate 42 for locating and securely retaining the cathode wire in its coaxial position with respect to the anode sleeve 37.

The positive potential corona energizing conductor 20 extends through a headed insulating sleeve 46 centrally located at the outer end of flexible conduit connector fitting 30 to terminate in electrical connection with a metal connector ferrule 47, such as by soldering. It will therefore be understood that when the corona discharge sensing tip assembly 10 is screwed in place upon the connector fitting 30, abutment contact between central contactor ferrules 47 and 40 serves to complete the positive potential energizing circuit to the anode sleeve 37. At the same time, negative corona energizing potential is applied through the outer metal casing of the flexible conduit 12, the outer body of the threaded male connector fitting 30, the metal tubular outer shell 21, the rectangular metal plate 42 of the cathode assembly which is in electrical abutting contact with the interior anular portions of said shell, to the cathode wire 43.

Operation of the above described halogen or freon gas sensor is as follows: A potential difference in the order of 1500 to 2000 VDC is established across the electrode pair 37, 43 so as to produce an electrical discharge in the continuous corona region. The sharpened wire emitter 43 is thus made more negative than the cylindrical electrode or anode sleeve 37. The discharge current which is measured by micro-ammeter 48 is in the vicinity of 10 microamperes D.C. As soon as the corona discharge is established, an air stream is produced by the negative ions which are being forced away from the highly stressed cathode wire 43; this air stream flows from cathode to anode, in effect suctioning air through the wire mesh screen in the front of the outer shell, around the corona discharge, through the anode sleeve 37 and out the vent holes 31 at the rear of the said shell. The magnitude of this air flow depends on the discharge current, on how far the sharp end of the cathode wire 43 is inside the anode sleeve and on the diameter of the anode sleeve.

Through experimental methods and using the basic configuration described above, it was determined that a tubular anode 37 having a 0.250" inside diameter and a length of 0.400" allowed the best air flow rate while keeping the overall sensor within practical size limitations. It was also observed that the position of the tip of the wire electrode 43 with respect to the tubular anode 37 made a significant difference in the flow rate and, also, in the characteristics of the corona. In general, the further inside the anode the wire is placed, the lesser the flow. A qualitative explanation of this phenomenon may be that when placed inside of the anode, the lines of force of the electric field tend to bend towards the back of the wire cathode electrode; the further the wire is placed inside the anode, the more they bend back. Since the air flow tends to follow the direction of the lines of force, the more these diverge the less of an axial flow will be produced. Tests showed that if the tip of the wire cathode is within 0.050" to 0.100" inside the cylindrical anode, the fastest flow was produced while maintaining a stable corona. Moreover, this suction flow or pumping action is self-regulating in the sense that it is greatest in clean air and diminishes when the halogen gas is sensed, eliminating the turbulence and dilution problems present in mechanical pumping systems. Since the mechanical pump is eliminated, the overall reliability of a system incorporating the above-described sensor is increased and a substantial reduction in size, weight and power consumption is realized. Finally, the sensitivity, efficiency and noise figure are greatly improved.

As pointed out above, the flow rate varies with the concentration of halogen gas in the air surrounding the discharge. This is due to the fact that the intensity of the "Ion Wind" is a direct function of the current density of the corona; since the corona current diminishes in direct proportion to the halogen gas concentration, so does the air flow diminish.

An important advantage of the invention resides in the provision of a practical sensor for halogen gases employing the negative corona principle of detection which takes advantage of the "Ion Wind" generated by the discharge to accurately direct the gas sample to the corona, ensuring that virtually every molecule of halogen gas impurity comes in contact with the discharge for dependable and sensitive freon or halogen gas leakage detection.

While I have illustrated and described herein only one form in which my invention can conveniently be embodied in practice, it is to be understood that this embodiment is presented by way of example only and not in a limiting sense. The invention, in brief, comprises all the embodiments and modifications coming within the scope and spirit of the following claims.

What I claim as new and desire to secure by Letters Patent is:

1. The method of automatically effecting a continuous flow of an air sample to be sensed for halogen gas contamination in a corona discharge detector of the type having a pair of mutually-spaced corona electrodes defining a corona electrode gap, one of which is sharply pointed, an electrical potential applied to the electrodes to establish a discharge corona therebetween in the continuous conrona region, and means for measuring changes in the corona current as an indication of halogen gas contamination, comprising; enclosing within an enclosure the discharge corona along the axis of the corona electrode gap so as to constrain the flow of air to be sensed for contamination along the path of current flow of the corona through the enclosure, highly electrically stressing the sharply pointed electrode with respect to the other electrode by virtue of the applied potential, providing openings at each end of the enclosure, placing the point of said sharply pointed electrode near one end of the enclosure to permit a flow of air to be sensed through the corona under the influence of the "ion wind" created by the highly stressed pointed electrode in the ionic flow from the highly stressed pointed electrode to the other electrode.

2. In a negative corona discharge halogan gas detector of the type having cathode and anode electrodes, an electrical potential applied to the electrodes to establish a corona discharge therebetween in the continuous corona region, and means for measuring changes in the corona current as an indication of halogen gas contamination in an air sample being detected or sensed, the combination comprising; a sharply pointed cathode electrode, an anode electrode spaced from said cathode electrode to define therewith a corona gap wherein said cathode will be highly electrically stressed to produce a corona discharge, said anode comprising a two-ended enclosure open at each end, means for constraining therethrough the flow of atmospheric air to be sensed along the path of ionic flow from said cathode in the corona discharge, said ionic flow, by virtue of the "ion wind" effect, serving to produce a continuous flow or "pumping action" of the atmosperic air being sensed through said enclosure for halogen gas contamination.

3. A negative corona discharge halogen gas detector as defined in claim 2, wherein said anode electrode is of tubular configuration, wherein said sharply pointed cathode electrode lies along the axis of symmetry of said tubular anode electrode near one end thereof, and wherein said means for constraining the flow of atmospheric air to be sensed comprises the internal wall of said tubular anode.

4. A negative corona discharge halogen gas detector as defined in claim 3 wherein said sharply pointed cathode electrode is axially spaced slightly inwardly of one end of said tubular anode electrode.

5. A negative corona discharge halogen gas detector as defined in claim 3 wherein said means for constraining the flow of atmospheric air to be sensed further comprises an electrically-conductive tubular outer shell surrounding said tubular anode in coaxial relation with respect thereto, means for electrically insulating said outer shell from said tubular anode, said tubular outer shell extending forwardly of one end of said tubular anode and rearwardly of the other end of said tubular anode, said forwardly-extending end of said tubular shell defining an opening for ingress of the atmospheric air to be sensed, and said rearwardly-extending end of said tubular shell defining means for egress of the atmospheric air to be sensed, said electrically-conductive tubular outer shell constituting means for applying said electrical potential to said cathode.

6. A negative corona discharge halogen gas detector as defined in claim 5 wherein said means for electrically insulating said outer shell from said tublar anode comprises a tubular casing extending forwardly of one end of said tubular anode and rearwardly of the other end of said tubular anode and having electrically insulating properties, means at the forwardly-extending end of said casing for supporting said cathode electrode, and means at the other end of said tubular casing for conducting corona potential current to said tubular anode electrode.

7. A negative corona discharge halogen gas detector as defined in claim 6, wherein said cathode electrode is in the form of small diameter wire, and wherein said means for supporting said cathode further comprises abutment means for making electrical contact with said tubular outer shell.

8. A negative corona discharge halogen gas detector as defined in claim 7, wherein said cathode supporting means comprises a rectangular metal plate, said cathode wire being secured to and extending outwardly of one edge of said plate, and a pair of diametrically opposed slots in the forwardly-extending end of said casing, opposed marginal ends portions of the said metal plate being received and seated in said slots, outwardly projecting corner portions of said metal plate being in electrical abutting contact with outer end portions of said electrically conductive tubular outer shell, whereby said corona gap can be energized by the application of the corona discharge potential across said corona conducting means and said electrically conductive tubular outer shell.

* * * * *